United States Patent [19]

Carpentier et al.

[11] Patent Number: 5,061,277
[45] Date of Patent: Oct. 29, 1991

[54] FLEXIBLE CARDIAC VALVULAR SUPPORT PROSTHESIS

[75] Inventors: Alain Carpentier, Paris, France; Ernest Lane, Huntington Beach, Calif.

[73] Assignee: Baxter International Inc., Deerfield, Ill.

[21] Appl. No.: 243,226

[22] Filed: Sep. 2, 1988

Related U.S. Application Data

[63] Continuation of Ser. No. 893,679, Aug. 6, 1986, abandoned.

[51] Int. Cl.⁵ ............................................. A61F 2/24
[52] U.S. Cl. ...................................................... 623/2
[58] Field of Search ............................................. 623/2

[56] References Cited

U.S. PATENT DOCUMENTS

| | | | |
|---|---|---|---|
| 3,656,185 | 4/1972 | Carpentier | 623/2 |
| 4,042,979 | 8/1977 | Augell | 623/2 |
| 4,055,861 | 11/1977 | Carpentier | 623/2 |
| 4,164,046 | 8/1979 | Cooley | 623/2 |
| 4,204,283 | 5/1980 | Bellhouse et al. | 623/2 |
| 4,217,665 | 8/1980 | Bex | 623/2 |
| 4,261,342 | 4/1981 | Duo | 623/2 |
| 4,290,151 | 9/1981 | Massand | 623/2 |
| 4,306,319 | 12/1981 | Kaster | 623/2 |
| 4,489,446 | 12/1984 | Reed | 623/2 |

OTHER PUBLICATIONS

"Size and Motion of the Mitral Valve Annulus in Anesthetized Intact Dogs", *Journal of Applied Physiology*, Anastasios G. Tsakiris et al., vol. 30, No. 5, (May 1971), pp. 611–618.

"Prosthetic Rings and Accessories for Tricuspid and Mitral Valvuloplasty", Carpentier-Edwards, American Edwards Laboratories, 036-12/85-PCCV, pp. 1–8.

*Primary Examiner*—Randall L. Green
*Assistant Examiner*—David H. Willse
*Attorney, Agent, or Firm*—Michael C. Schiffer

[57] ABSTRACT

A support for a natural heart valve is disclosed. The support is generally ring shaped and has a size and shape to fit against the natural heart valve annulus. First length of the support is flexible, and a second length of the support is less flexible than the first length of the support. Accordingly, when the support is implanted, the support can shape the heart valve annulus and the first length of the support allows contraction of the heart valve annulus therealong.

18 Claims, 2 Drawing Sheets

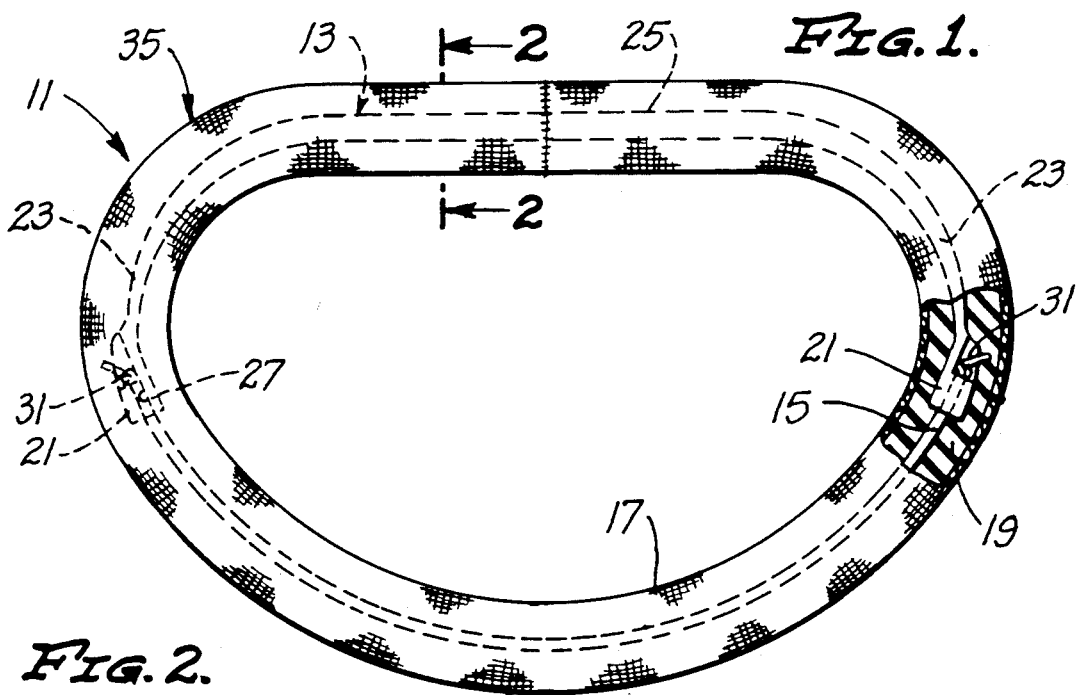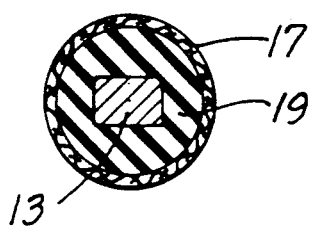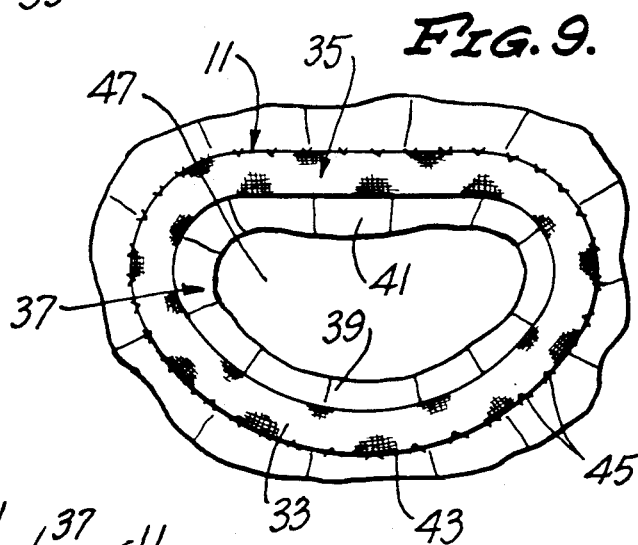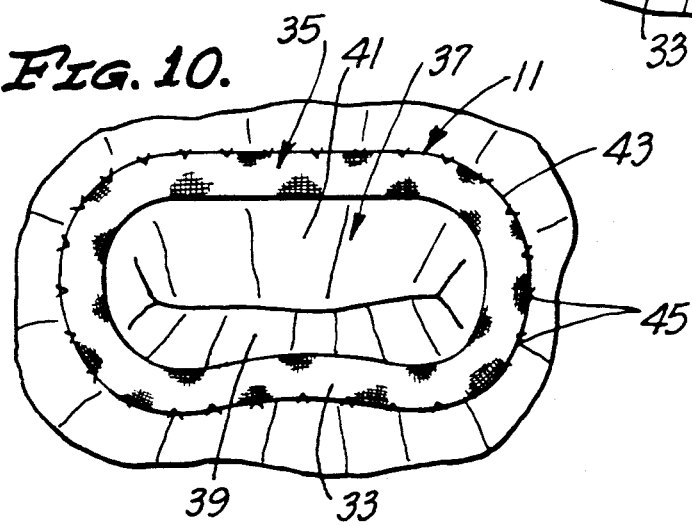

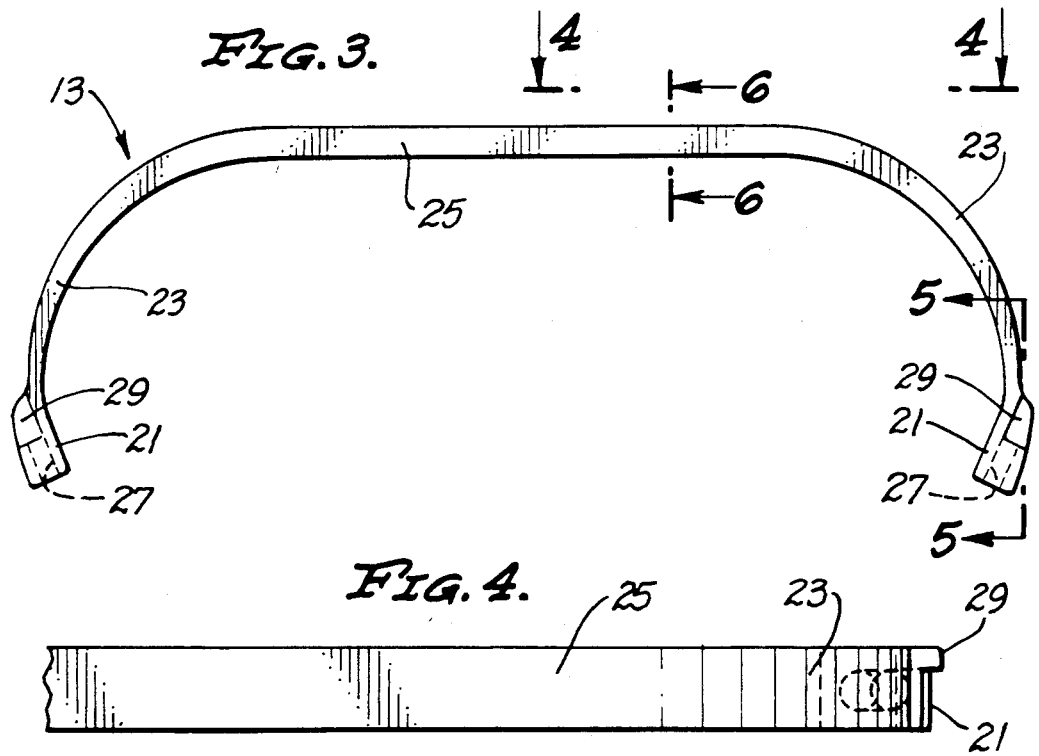
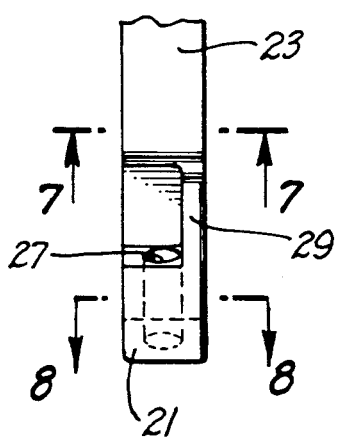
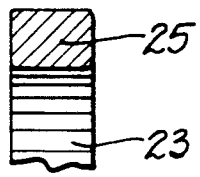
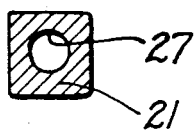

FLEXIBLE CARDIAC VALVULAR SUPPORT PROSTHESIS

This is a continuation of prior application Ser. No. 06/893,679, filed on Aug. 6, 1986, now abandoned.

BACKGROUND OF THE INVENTION

Human heart valves comprise leaflets or cusps which open and close to control the flow of blood to a particular region of the heart. For example, a mitral valve includes a posterior cusp and an anterior cusp, both of which are joined at their bases to a mitral valve annulus of the heart. The mitral valve is open during diastole and closed during systole.

When the mitral valve opens, its annulus dilates or distends, along the base of the posterior cusp and when the mitral valve closes, the mitral valve annulus contracts along the base of the posterior cusp to allow the cusps to come into apposition or sealing contact with each other. In some patients with diseased heart valves, the dilation of the annulus can become permanent, and the mitral valve annulus becomes distorted during systole. The permanent dilation of the annulus causes regurgitation, i.e. backflow of blood through the valve.

These conditions as well as certain others can be addressed by implanting a support in the heart along the valve annulus. A support of this type may be rigid as described in Carpentier U.S. Pat. No. 3,656,185 or flexible as described in Carpentier et al U.S. Pat. No. 4,055,861. The rigid support, although satisfactory for some applications, does not allow the valve annulus to contract along the base of the posterior cusp and accordingly, significant stress may be imposed on the sutures, and the valve may not operate in a completely natural way. The completely flexible support, although better able to conform to dynamic changes in shape of the annulus is less effective in restoring a physiologic shape of the annulus and preventing undesired distortion. Consequently, neither the rigid support nor the flexible support allow the valve to operate in a completely natural way.

SUMMARY OF THE INVENTION

This invention provides a novel heart valve support which is capable of pulling the annulus back to approximately the correct shape and which allows the annulus to properly contract. Accordingly, the stresses on the sutures and the leaflets are reduced and the valve operates in a more natural way. Although the features of this invention are applicable to various different heart valves, they are particularly adapted for a mitral valve.

The support of this invention is generally ring shaped and has a size and shape to fit against the natural heart valve annulus. The terms "ring shaped" and "ring shaped structure" as used herein mean any configuration which circumscribes or surrounds a region, and are not limited to, circular configurations.

One feature of this invention is that the support has differential flexibility along its length. More specifically, a first length of the support is flexible and a second length of the support is less flexible than the first length. The less flexible second length may be rigid or flexible and in a preferred construction, includes segments which are substantially rigid and which are somewhat, or slightly flexible. With this construction, the less flexible or more rigid second length is placed along a region of the annulus which must be subjected to more rigid control and the flexible first length is placed on a region of the annulus which must be allowed to readily contract so that the flexibility of the flexible first length can accommodate such contraction. Thus, the differential flexibility of the support is tailored to the requirements of the annulus. As applied to a mitral valve, the flexible first length preferably extends along the annulus at the base of the posterior cusp, which must be allowed to more fully contract, and the more rigid length of the support is placed along the anterior cusp for better control of this region of the annulus. Collectively, the first and second lengths are capable of pulling the annulus back to approximately its correct shape.

Although various constructions are possible, the support preferably includes an elongated frame member having opposite end portions and segments extending in different directions and a flexible cord coupled to the opposite end portions of the frame member to form a circumscribing structure which circumscribes a region. A flexible sheath at least partially encloses the frame member and the flexible cord to provide more softness and body compatability as well as to facilitate suturing of the support into the heart.

In order that the cord can accommodate movement of the annulus, there is slack in the cord. More specifically, the length of the cord between the opposite end portions of the frame member is greater than is required to extend in a straight line between the opposite end portions of the frame member. So that the cord will be effective in pulling the annulus back to its correct shape, it is preferably essentially non-distensible.

The support may also include a soft compressible material within the sheath. This material, which may be radiaopaque, is useful in suturing the support into the heart and provides the support with a soft quality. It also can be used to prevent relative movement between the cord and the frame member which would cause abrasion to the cord at the region of attachment of the cord to the frame member.

In a preferred construction, the frame member is constructed of metal and includes first and second curved segments joined by an essentially straight segment. All of these segments lie in substantially the same plane and the curved segments extend away from the straight segment in generally the same direction. Regions of the first and second curved segments are of progressively reducing cross-sectional area as they extend distally so that such distal regions of the frame member are more flexible or less rigid. The straight segment may be essentially rigid.

The invention, together with additional features and advantages thereof may best be understood by reference to the following description, taken in connection with the accompanying illustrative drawing.

BRIEF DESCRIPTION OF THE DRAWING

FIG. 1 is a plan view, partially in section, of one form of support constructed in accordance with the teachings of this invention.

FIG. 2 is a sectional view taken generally along line 2—2 of FIG. 1.

FIG. 3 is a top plan view of a preferred form of frame member.

FIG. 4 is an enlarged fragmentary view taken generally along line 4—4 of FIG. 3.

FIGS. 5 and 6 are views taken generally along lines 5—5 and 6—6, respectively of FIG. 3.

FIGS. 7 and 8 are sectional views taken generally along lines 7—7 and 8—8, respectively, of FIG. 5.

FIGS. 9 and 10 show the support implanted in a natural mitral heart valve with the valve being in diastole and systole, respectively.

DESCRIPTION OF THE PREFERRED EMBODIMENT

FIG. 1 shows a support 11 which generally includes a frame member 13 (FIG. 3), a cord 15, a sheath 17 and soft compressible material 19 within the sheath and surrounding the full length of the frame member and cord. The support 11 lies essentially in the same plane, and it is generally ring-shaped. The support 11 has a size and shape to fit against the natural mitral heart valve annulus of a human.

Although various constructions are possible, the frame member 13 in this embodiment is constructed of a biocompatible metal, such as titanium 6A1-4V and is elongated and has opposite end portions. The elongated frame member lies in a single plane and includes curved segments 23 integrally joined by a segment 25. The curved segments 23 extend away from the straight segment 25 in the same general direction such that the frame member 13 is somewhat channel-like. In this embodiment, the curved segments 23 are identical, generally circular segments which extend for about 120° and terminate in the end portions 21. Although various different cross sectional configurations can be employed, in this embodiment, the frame member 13 is of a generally rectangular cross-sectional configuration throughout most of its length with the thickness of the cross-section being greater in the straight segment 25 (FIG. 6) than it is in the curved segments 23 (FIG. 7). To keep stresses more even throughout the curved segments, preferably the curved segments 23 are of a progressively reducing cross sectional area as they extend distally until they reach the end portions 21, which are enlarged. With this construction, the straight segment 25 is essentially rigid and the curved segments 23 are of progressively increasing flexibility or reduced rigidity as they extend distally to the end portions 21.

The end portions 21, which may be identical, form the distal regions of the curved segments 23. Each of the end portions 21 is of enlarged cross-section as shown in FIGS. 3 and 8 and includes a passage 27 extending therethrough. The passages 27 terminate proximally at lateral flanges 29.

The cord 15 is flexible and may be, for example, constructed of a suitable biocompatible, braided or woven material, such as Dacron. The opposite ends of the cord 15 are attached to the opposite end portions 21 of the frame member 13 in any suitable manner, such as by extending the cord through the passage 27 of the end portion and forming a knot 31 of a size too large to pass through the passage 27.

The cord 15 is longer than is necessary to simply extend in a straight line between the end portions 21. In this embodiment, the cord 15 is formed into an arc by the soft material 19 which completely encases the cord and the frame member 13. The soft material 19 is biocompatible and may be, for example, silicone rubber containing, for example, barium sulfate, if desired, to make it radiopaque. The material 19 makes the entire support 11 soft and compressible, and it gives a flexible length 33 of the support along the cord 15 between the end portions 21 resilence while holding the length 33 in an unstressed accurate configuration as shown in FIG. 1. Thus, although the length 33 normally is in the shape shown in FIG. 1, it can readily be moved radially inwardly in response to a radial inward force, and when the force is removed, it returns to the shape shown in FIG. 1. The material 19 also prevents relative abrasive movement of the cord 15 and frame member 13 at the passages 27.

The cord 15 is essentially nondistensible. When the cord 15 is coupled to the end portions 21 of the frame member 13, the cord and frame member completely circumscribe a region.

The flexible sheath 17 in this embodiment is in the form of a fabric jacket which completely encloses the soft material 19, the cord 15 and the frame number 13. For example, the sheath 17 may be constructed of knitted Dacron cloth.

When so constructed, the length 33 is resiliently flexible and a length 35 of the support 11, which is co-extensive in length with the frame member 13, is less flexible than the length 33. In fact, the length of the support 11 along the straight segment 25 may be considered as essentially rigid and distal regions of the length 35 along the curved segments 23 are of progressively increasing flexibility as they extend distally. Thus, such distal regions are somewhat resiliently flexible, but much more rigid than the length 33.

The support 11 is adapted for use with a mitral heart valve 37 (FIGS. 9 and 10). The mitral heart valve has a posterior cusp 39, an anterior cusp 41 and an annulus 43 circumscribing the cusps 39 and 41 adjacent the bases of the cusps.

The support 11 can be sutured to the annulus 43 using sutures 45 as shown in FIGS. 9 and 10 such that the flexible length 33 extends generally along the annulus 43 at the base of the posterior cusp 39 and the less flexible length 35 extends along the annulus at the base of the anterior cusp 41. The sutures 45 extend through the sheath 17 and the soft material 19 which combine to serve as a sewing ring for the support 11. The suturing of the support 11 to the annulus 43 pulls the annulus 43 back to approximately its correct shape.

As shown in FIG. 9, during diastole, the valve cusps 39 and 41 are separated to form an opening 47. During this time, the annulus 43 tends to distend radially outwardly or dilate along the base of the posterior cusp 39. During systole, the cusps 39 and 41 close to close the opening 47. During systole, the annulus 43 contracts along the base of the posterior cusp 39. The flexible length 33 can be readily moved radially inwardly by the contracting adjacent regions of the annulus 43 to readily accommodate this contraction. Consequently, stress on the sutures 45 and on the cusps 39 and 41 is minimized. Accordingly, the support 11 correctly shapes the annulus 43 while allowing the normal, but very pronounced contraction of the annulus along the base of the posterior cusp 39.

Although an exemplary embodiment of the invention has been shown and described, many changes, modifications and substitutions may be made by one having ordinary shill in the art without necessarily dearting from the spirit and scope of this invention.

We claim:

1. An annuloplasty ring prosthesis for suturing about a heart valve orifice comprising:
    a rigid frame member dimensioned to extend about a portion of said valve orifice, said frame member having first and second opposing ends;

an elongated flexible member connected between said frame member ends;
a flexible sheath means formed about said rigid frame member and said elongated flexible member; and
soft compressible, resilient material filling said flexible sheath means about at least said flexible member.

2. A ring prosthesis as defined in claim 1 wherein said rigid frame member is a metal frame member.

3. A ring prosthesis as defined in claim 2 wherein said flexible member is a flexible cord.

4. A ring prosthesis comprising:
an elongated frame member formed with a substantially straight portion having opposing ends which are curved towards one another;
a flexible member secured to and between said frame member curved ends;
a sheath formed about said frame and flexible members; and
a soft, compressible material filling said sheath about said frame and flexible members.

5. A ring prosthesis as defined in claim 4 wherein said soft compressible material is positioned within the sheath between the flexible member and the sheath and the frame member and the sheath.

6. A ring prosthesis as defined in claim 5 wherein the length of the flexible member between said opposing ends of the frame member is greater than is required to extend in a straight line between said ends of the frame member.

7. A ring prosthesis as defined in claim 6 wherein the compressible material forms the flexible member into an arc between said ends of the frame member.

8. A ring prosthesis as defined in claim 7 wherein the flexible member is essentially nondistensible.

9. The ring prosthesis of claim 4 wherein said flexible member is a cord.

10. A ring prosthesis as defined in claim 9 wherein the length of the cord between said opposing ends of the frame member is greater than is required to extend in a straight line between said opposing ends of the frame member, and wherein said soft compressible material encapsulating the cord forms the cord into an arc between said opposing ends of the frame.

11. An annuloplasty ring prosthesis for suturing about a heart valve orifice comprising:
a substantially oval shaped body portion having a first rigid elongated portion which is formed to lie about a substantial portion of said heart valve, which rigid portion is formed with two opposing ends and an elongated resilient and elastic member connected to and disposed between said opposing ends of said rigid portion to lie about the remainder of said heart valve, wherein said resilient and elastic member is less rigid than said rigid elongated portion
a flexible enclosure means formed about said rigid elongated portion and said elongated flexible and elastic member, said enclosure means being further formed with a portion to allow suturing of said prosthesis about said heart valve.

12. A ring prosthesis as defined in claim 11 wherein distal regions of said rigid portion are of progressively increasing flexibility as they extend distally.

13. A ring prosthesis as defined in claim 12 wherein the rigid portion includes first and second curved segments joined by an essentially straight segment, said curved segments and said straight segment are in substantially the same plane and said curved segments extend away from the straight segment in the same general direction.

14. A ring prosthesis as defined in claim 13 wherein regions of the first and second curved segments are of progressively reducing cross sectional area as they extend distally.

15. A support for a heart valve comprising:
an elongated frame member forming a portion of a ring and having opposite end portions;
a flexible cord coupled to the opposite end portions of the frame member and extending continuously between said end portions to form a structure which circumscribes a region, said support being implantable to support a human heart valve annulus; and
a soft, compressible, resilient material extending along the cord and shaping the cord between the end portions of the frame member.

16. A support as defined in claim 15 including a flexible sheath at least partly enclosing the frame member, the flexible cord and the resilient material.

17. A support as defined in claim 15 wherein the compressible material forms the cord into an arc between said opposite end portions of the frame member and the cord is essentially nondistensible.

18. A support as defined in claim 17 wherein the frame member includes first and second curved segments joined by an essentially straight segment, said curved segments and said straight segment are in substantially the same plane, said curved segments extend away from the straight segment in the same general direction, regions of the first and second curved segments are of progressively reducing cross sectional area as they extend distally and the support includes a flexible sheath at least partially enclosing the frame member, the flexible cord and the sheath.

* * * * *

REEXAMINATION CERTIFICATE (4002nd)

United States Patent [19]
Carpentier et al.

[11] B1 5,061,277
[45] Certificate Issued Feb. 29, 2000

[54] FLEXIBLE CARDIAC VALVULAR SUPPORT PROSTHESIS

[75] Inventors: Alain Carpentier, Paris, France; Ernest Lane, Huntington Beach, Calif.

[73] Assignee: Baxter Travenol Laboratories, Inc., Deerfield, Ill.

Reexamination Request:
No. 90/004,850, Nov. 28, 1997

Reexamination Certificate for:
Patent No.: 5,061,277
Issued: Oct. 29, 1991
Appl. No.: 07/243,226
Filed: Sep. 2, 1988

Related U.S. Application Data

[63] Continuation of application No. 06/893,679, Aug. 6, 1986, abandoned.

[51] Int. Cl.$^7$ .................................................. A61F 2/24
[52] U.S. Cl. ............................................................ 623/2
[58] Field of Search ................................................ 623/2

[56] References Cited

FOREIGN PATENT DOCUMENTS 577022  10/1977  U.S.S.R. .

*Primary Examiner*—D. Willse

[57] ABSTRACT

A support for a natural heart valve is disclosed. The support is generally ring shaped and has a size and shape to fit against the natural heart valve annulus. First length of the support is flexible, and a second length of the support is less flexible than the first length of the support. Accordingly, when the support is implanted, the support can shape the heart valve annulus and the first length of the support allows contraction of the heart valve annulus therealong.

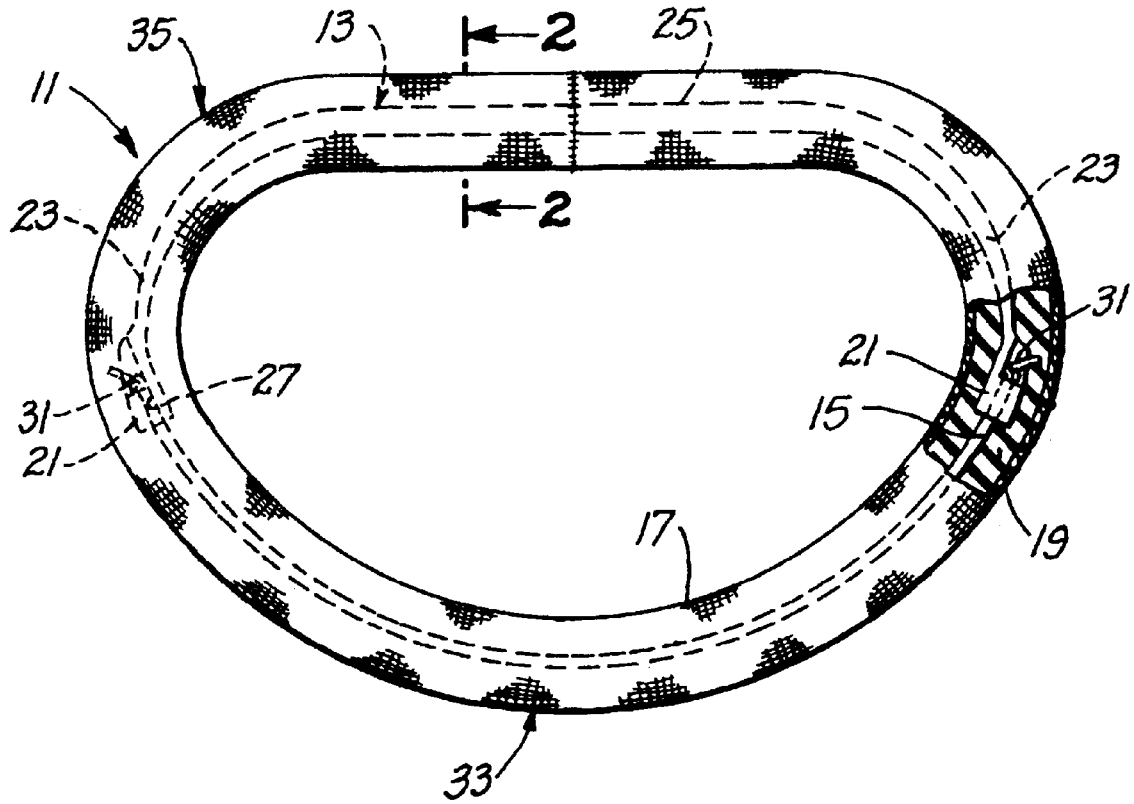

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 8, 12, and 17 are cancelled.

Claims 1, 4, 11, 13, 15, and 18 are determined to be patentable as amended.

Claims 2, 3, 5–7, 9, 10, 14, and 16, dependent on an amended claim, are determined to be patentable.

New claims 19–21 are added and determined to be patentable.

1. An annuloplasty ring prosthesis for suturing about a heart valve orifice comprising:
   a rigid frame member dimensioned to extend about a portion of said valve orifice, said frame member having first and second opposing ends;
   an elongated flexible member connected between said frame member ends, *wherein said elongated flexible member is essentially nondistensible*;
   a flexible sheath [means] formed about said rigid frame member and said elongated flexible member; and
   soft compressible, resilient material filling said flexible sheath [means] about at least said flexible member.

4. A ring prosthesis comprising:
   an elongated frame member formed with a substantially straight portion having opposing ends which are curved towards one another;
   a flexible member secured to and between said frame member curved ends, *wherein said flexible member is essentially nondistensible*;
   a sheath formed about said frame and flexible members; and
   a soft, compressible material filling said sheath about said frame and flexible members.

11. An annuloplasty ring prosthesis for suturing about a heart valve orifice comprising:
    a substantially oval shaped body portion having a first rigid elongated portion which is formed to lie about a substantial portion of said heart valve, which rigid portion is formed with two opposing [ends] *distal regions being of progressively increasing flexibility as they extend distally and each of which terminates at an end portion thereof,* and an elongated resilient [and], *flexible,* elastic [member] *and essentially non distensible portion* connected to and disposed between said opposing [ends] *end portions* of said rigid portion to lie about the remainder of said heart valve, wherein said resilient, *flexible,* [and] elastic [member] *and essentially nondistensible portion* is less rigid than said rigid elongated portion;
    a flexible [enclosure means] *sheath* formed about said rigid elongated portion and said elongated *resilient, flexible* [and]*,* elastic [member] *and essentially nondistensible portion,* said [enclosure means] *flexible sheath* being further formed with a portion to allow suturing of said prosthesis about said heart valve.

13. A ring prosthesis as defined in [claim 12] *claims 11 or 20* wherein the rigid portion includes first and second curved segments joined by an essentially straight segment, said curved segments and said straight segment are in substantially the same plane and said curved segments extend away from the straight segment in the same general direction.

15. A support for a heart valve comprising:
    an elongated frame member forming a portion of a ring and having opposite end portions;
    a flexible cord coupled to the opposite end portions of the frame member and extending continuously between said end portions to form a structure which circumscribes a region, *said flexible cord being essentially nondistensible and* said support being implantable to support a human heart valve annulus; and
    a soft, compressible, resilient material extending along the cord and shaping the cord between the end portions of the frame member.

18. A support as defined in claim [17] *16* wherein the frame member includes first and second curved segments joined by an essentially straight segment, said curved segments and said straight segment are in substantially the same plane, said curved segments extend away from the straight segment in the same general direction, regions of the first and second curved segments are of progressively reducing cross sectional area as they extend distally [and the support includes a flexible sheath at least partially enclosing the frame member, the flexible cord and the sheath].

*19. An annuloplasty ring prosthesis for suturing about a heart valve orifice comprising:*
   *a substantially oval shaped body portion having a first rigid elongated portion which is formed to lie about a substantial portion of said heart valve, which rigid portion is formed with two opposing end portions, and an elongated resilient, flexible, elastic and essentially non distensible portion connected to and disposed between said opposing end portions of said rigid portion to lie about the remainder of said heart valve, wherein said resilient, flexible, elastic and essentially nondistensible portion is less rigid than said rigid elongated portion;*
   *a flexible sheath formed about said rigid elongated portion and said elongated resilient, flexible, elastic and essentially nondistensible portion, said flexible sheath being further formed with a portion to allow suturing of said prosthesis about said heart valve.*

*20. An annuloplasty ring prosthesis for suturing about a heart valve orifice comprising;*
   *a substantially oval shaped body portion having a first rigid elongated portion which is formed to lie about a substantial portion of said heart valve, which rigid portion is formed with two opposing distal regions being of progressively increasing flexibility as they extend distally and each of which terminates at an end portion thereof, and an elongated resilient, flexible, elastic portion connected to and disposed between said opposing end portions of said rigid portion to lie about the remainder of said heart valve, wherein said resilient, flexible, elastic portion is less rigid than said rigid elongated portion;*
   *a flexible sheath formed about said rigid elongated portion and said elongated resilient, flexible, elastic* portion, said flexible sheath being further formed with a portion to allow suturing of said prosthesis about said heart valve.

21. A ring prosthesis as defined in claim 20 wherein said two opposing distal regions are comprised of progressively reducing cross sectional areas as said opposing distal regions extend distally.

* * * * *